(12) United States Patent
Edwards et al.

(10) Patent No.: US 10,016,467 B2
(45) Date of Patent: Jul. 10, 2018

(54) FORMULATIONS OF VIABLE CELLS FOR ORAL DELIVERY

(75) Inventors: Alexander Edwards, Cambridge (GB); Nigel Slater, Cambridge (GB)

(73) Assignees: Cambridge Enterprise Limited, Cambridge (GB); Prokarium Limited, Keele (GB)

( * ) Notice: Subject to any disclaimer, the term of this patent is extended or adjusted under 35 U.S.C. 154(b) by 221 days.

(21) Appl. No.: 13/143,829

(22) PCT Filed: Jan. 11, 2010

(86) PCT No.: PCT/GB2010/000035
§ 371 (c)(1),
(2), (4) Date: Sep. 28, 2011

(87) PCT Pub. No.: WO2010/079343
PCT Pub. Date: Jul. 15, 2010

(65) Prior Publication Data
US 2012/0027811 A1 Feb. 2, 2012

(30) Foreign Application Priority Data
Jan. 9, 2009 (GB) .................................. 0900350.0

(51) Int. Cl.
*A61K 35/74* (2015.01)
*A61K 9/20* (2006.01)
*A61K 9/50* (2006.01)

(52) U.S. Cl.
CPC ............ *A61K 35/74* (2013.01); *A61K 9/2027* (2013.01); *A61K 9/5036* (2013.01)

(58) Field of Classification Search
None
See application file for complete search history.

(56) References Cited

U.S. PATENT DOCUMENTS 2,811,492 A * 10/1957 Gustus ............................ 521/37
3,383,281 A * 5/1968 Tennent ............... A61K 31/785
424/78.12
5,482,718 A * 1/1996 Shah et al. .................... 424/480
(Continued)

FOREIGN PATENT DOCUMENTS

EP 1 281 752 A1 2/2003
EP 1 421 945 A1 5/2004
(Continued)

OTHER PUBLICATIONS

Masschalck et al. "Antimicrobial properties of lysozyme in relation to foodborne vegetative bacteria," Critical Reviews in Microbiology 29(3):191-214, 2003.*
(Continued)

*Primary Examiner* — Ileana Popa
*Assistant Examiner* — Alissa Prosser
(74) *Attorney, Agent, or Firm* — Foley Hoag LLP (57) ABSTRACT

This invention relates to solid formulations for the oral delivery of live microbial cells which comprise dried viable cells and small amounts of a bile acid binding agent, for example, an anion exchange resin such as cholestyramine. The presence of bile acid binding agents in the formulation significantly increases the survival of the cells in the intestinal tract and facilitates delivery of the viable cells to the intestine.

13 Claims, 8 Drawing Sheets

(56) References Cited

U.S. PATENT DOCUMENTS

| | | | |
|---|---|---|---|
| 5,942,242 A | 8/1999 | Mizushima et al. | |
| 2006/0093591 A1* | 5/2006 | Farmer et al. | 424/93.45 |
| 2008/0124355 A1* | 5/2008 | Bermudes | 424/200.1 |

FOREIGN PATENT DOCUMENTS

| | | | |
|---|---|---|---|
| GB | 825480 A | | 12/1959 |
| JP | 2003235501 A | | 8/2003 |
| JP | 2004250338 A | | 9/2004 |
| WO | WO-97/41741 A1 | | 11/1997 |
| WO | WO-2004/076657 A2 | | 9/2004 |
| WO | WO-2007/079147 A2 | | 7/2007 |
| WO | WO-2007/140613 A1 | | 12/2007 |
| WO | WO 2011/026111 | * | 3/2011 |

OTHER PUBLICATIONS

Bullifent et al. "Stabilization of Salmonella vaccine vectors by the induction of trehalose biosynthesis," Vaccine 19:1239-1245, 2001.*
Miyao (JP 2004-250338, published Sep. 9, 2004, IDS reference filed Jun. 8, 2012) JPO machine translation, 2013.*
Online product information for Lysozyme from Thermo Scientific dated 2013; http://www.piercenet.com/browse.cfm?fldID=3C6EACCB-232E-44DC-913F-6D9B16BEF8D5.*
George et al. "Polyionic hydrocolloids for the intestinal delivery of protein drugs: alginate and chitosan—a review" Journal of Controlled Release 114:1-14, 2006.*
Neutra et al., "Mucosal vaccines: the promise and the challenge," Nature Reviews Immunology 6:148-158, 2006.*
Wikipedia entry for "Enterohepatic circulation," last modified May 24, 2015; https://en.wikipedia.org/wiki/Enterohepatic_circulation.*
McConnell et al., "Colonic antigen administration induces significantly higher humoral levels of colonic and vaginal IgA, and serum IgG compared to oral administration," Vaccine 26:639-646, 2008, available online Dec. 18, 2007.*
Dobson, "On the presence of Peyer's patches (Glandulae Agminatae) in the caecum and colon of certain mammals," Journal of Anatomy and Physiology 18(Pt 4):388-392, 1884.*
Nicoletti, "Unsolved mysteries of intestinal M cells," Gut 47:735-739, 2000.*
Krasopoulos et al. "The adsorption of bile salts on activated carbon," Lipids 15(5):365-370, 1980.*
Nakano et al. "In vitro adsorption characteristics of bile salt anions by activated carbon beads for oral administration," Chemical and Pharmaceutical Bulletin 32(10):4096-4102, 1984.*
Vahouny et al. "Dietary Fibers: V. Binding of bile salts, phospholipids and cholesterol from mixed micelles by bile acid sequestrants and dietary fibers," Lipids 15(12):1012-1018, 1980.*
Auerbach "Typhoid fever vaccine," published online Jun. 7, 2008; http://www.healthline.com/health-blogs/outdoor-medicine/typhoid-fever-vaccine.*
Partial USPTO translation of JP 2004-250338, paragraphs 22, 24 and 25, tables 1 and 2, 2017.*
Story et al. "Comparison of the binding of various bile acids and bile salts by several types of fiber," Journal of Nutrition 106:1292-1294, 1976.*
Begley et al. "The interaction between bacteria and bile," FEMS Microbiology Reviews 29:625-651, 2005.*
Edwards, Alexander, D., et al. "Formulation of a live bacterial vaccine for stable room temperature storage results in loss of acid, bile and bile salt resistance", Vaccine, 26(45): 5675-5678 (2008).
Edwards, Alexander, D., et al. "Protection of live bacteria from bile acid toxicity using bile acid absorbing resins", Vaccine, 27(29):3897-3903 (2009).
Ford, Robert, P., et al., "The effect of a rat plasma high-density lipoprotein subfraction on the synthesis of bile salts by rat hepatocyte monolayers", Elsevier Science Publishers B.V., Federation of European Biochemical Societies, 179(1):177-180 (1985).
International Search Report dated Aug. 7, 2010 from PCT/GB2010/000035.
Hashizume, et al., "Peyer's Patches Are Required for Intestinal Immunoglobulin A Responses to *Salmonella* spp," Infection and Immunity, 76(3):927-34 (Mar. 2008).
Jones, et al., "*Salmonella typhimurium* Initiates Murine Infection by Penetrating and Destroying the Specialized Epithelial M Cells of the Peyer's Patches," Journal of Experimental Medicine, 180(1):15-23 (Jul. 1, 1994).
Jung, et al., "Peyer's Patches: The Immune Sensors of the Intestine," International Journal of Inflammation, 2010:823710 (12 pgs.) (2010).
Penheiter, et al., "Non-invasive *Salmonella typhimurium* mutants are avirulent because of an inability to enter and destroy M cells of ileal Peyer's patches," Molecular Microbiology, 24(4):697-709 (1997).

* cited by examiner

FORMULATIONS OF VIABLE CELLS FOR ORAL DELIVERY

This invention relates to formulations for the oral delivery of viable cells, such as bacterial cells.

Oral live bacteria delivery is currently used in two main types of therapeutic application. Firstly, unmodified enteric bacteria strains identified from gut isolates are of therapeutic interest in re-colonisation of the intestine after antibiotic treatment [1], in symptomatic relief for sufferers of inflammatory intestinal disease [2], and also in genetically engineered forms for delivery of biological therapies (e.g. IL-10 [3]). Secondly, live bacteria are attractive candidate vaccines. Currently, a number of human clinical trials are in progress testing various strains of attenuated live bacteria for protection against diseases such as Cholera, enterotoxic *E. coli* and Typhoid fever ([4]). Live bacterial vaccines have the advantage over conventional vaccines that they are administered orally, avoiding injections and needles. Genetically engineered live bacterial vaccines may also carry heterologous DNA or antigens from pathogens or tumours to stimulate or prime immune responses against pathogen or tumour cells.

Bacteria for live delivery are generally dried for stability reasons. The alternative to dry formulation for live bacterial delivery is a 'wet' format, e.g. a food product such as yoghurt. Live bacteria have significant stability problems in liquid forms, even if refrigerated. A number of microencapsulation systems have been proposed for oral delivery of bacteria [5], but all suffer from the same issue of degradation of the bacteria during storage, and a requirement for costly refrigeration to reduce degradation.

Various techniques for producing dried bacteria are known in the art. Most commonly, conventional freeze-drying is used. In addition, there has been recent focus on the use of di-saccharides such as trehalose and sucrose, which stabilise biomolecules and make dried bacteria more stable at room temperature [6], [7]. Disaccharide-stabilised dry bacteria, for example, may be conveniently stored at room temperature.

Currently, dried live bacteria are administered orally in two common formats: enteric capsules of freeze-dried bacteria, and sachets of freeze-dried bacteria to be resuspended in a bicarbonate buffer. Often, very high doses of bacteria are given, and multiple doses are needed to give only modest effects. Interestingly, clinical data indicates that the enteric capsule formulation is significantly less effective than the bicarbonate buffer system [8][15], although little is known about why the enteric capsules are relatively ineffective.

Little is known about the mechanism of action of the bicarbonate buffer system. The quantity of bicarbonate buffer swallowed is not likely to absorb the acid secreted into the stomach, and so it seems likely that bacteria administered in this way will encounter some acidity. In spite of these potential limitations, co-administration with bicarbonate buffer or similar acid neutralising buffer is currently the standard mode of delivery in ongoing human clinical trials of vaccine strains for diseases such as Cholera [9] and Enterotoxic *E. coli* [10].

The stomach has the ability to secrete hydrochloric acid and reduce the contents below pH 1. Few bacteria can survive to this pH [11] and dried live bacteria have been shown to be even more sensitive than bacteria from fresh cultures [12]. An 'enteric' coating may be used to avoid the death of the live bacterial formulations in gastric acid. An enteric coating is a polymer layer that will not dissolve in acidic conditions, but will dissolve in the intestine after stomach emptying, releasing the dry bacteria into the upper small intestine. As noted above, existing enteric capsules of a live bacterial vaccine are relatively ineffective, in spite of their ability to protect bacteria from stomach acid [8].

The intestine contains a complex mixture of enzymes and other microbicidal agents. Bile is secreted into the duodenum from the gall bladder. Bile generally comprises at least 50% bile acids, which act as detergents to dissolve and digest fatty food components. Bile acids are also potent at killing bacteria. Bacterial strains that typically reside in intestinal sites, such as *Salmonella* spp, have evolved resistance mechanisms to detergents such as bile salts, allowing them to survive and grow in the intestine.

Bacteria generally lose their resistance to bile acids after drying or freezing. Dried bacteria which are released into the intestine from an enteric formulation are sensitive to bile acids and do not survive in the intestinal environment [12].

The present invention relates to the finding that the incorporation of small amounts of bile acid binding agents into formulations of dried viable cells significantly increases the survival of the cells in the intestinal tract. These formulations may therefore be useful for the oral delivery of live cells, such as bacterial cells, to the intestine.

An aspect of the invention provides a solid formulation for oral administration to an individual, which comprises dried viable cells and a bile acid binding agent.

The bile binding agent allows aqueous liquids to permeate the formulation but absorbs bile acids and retards their permeation through the formulation. This protects the dried viable cells from bile acid toxicity until they are rehydrated by the permeating aqueous liquid and recover their bile tolerance. This may, for example, increase the efficacy of delivery of the cells to the intestine.

The dried viable cells may be microbial cells. Any microbial cell may be employed in the formulations described herein and the type or types of cell will depend on the particular purpose for which the formulation is used.

In some embodiments, bacterial cells may be employed, for example cells from enteric bacterial species. Enteric bacteria are well-known in the art and include pathogen and non-pathogenic species, for example, Enterobacteriaceae such as *Escherichia, Salmonella, Klebsiella, Enterobacter, Serratia, Proteus* spp, and also *Bifidobacterium, Bacteroides, Clostridium, Pseudomonas, Ruminococcus, Lactobacillus, Lactococcus, Campylobacter*, and *Streptococcus* spp.

The delivery of enteric bacterial cells to the intestine using the formulations described herein may be useful, for example, in restoring the gut flora of a patient, e.g. after antibiotic treatment, and in the symptomatic relief of patients with inflammatory intestinal disease.

In other embodiments, the dried viable microbial cells may be eukaryotic cells, for example yeast or fungal cells such as *Saccharomyces, Aspergillus* spp or *Candida* spp.

In some embodiments, microbial cells with specific enzymatic or other properties may be employed. The delivery of such cells to the intestine may be useful, for example, in the breakdown or metabolism of disease associated compounds or toxins, such as oxalate, which is a risk factor for renal stone formation, or in reducing cholesterol levels, by influencing intestinal absorption.

In some embodiments, the microbial cells may express a therapeutic factor, such as a recombinant protein. Suitable recombinant polypeptides may be exogenous to the bacterial cell (i.e. a polypeptide not naturally expressed by the bacterial cell, such as a human polypeptide), and may have a therapeutic effect on the patient. Suitable recombinant polypeptides include cytokines, including interleukins such as IL-10; chemokines; and antibodies, antibody fragments or related binding molecules that bind to mediators of the immune response, such as cytokines (e.g. to neutralise TNF-alpha in inflammatory bowel diseases).

Suitable microbial cells for expression of recombinant polypeptides include cells from lactic acid bacterial species, e.g. Lactococci such as *L. lactis* (European Journal of Pharmaceutics and Biopharmaceutics (2005) 60:349), Enterobacteriaceae and other enteric bacteria as described above, and other microbial cells such as yeasts and fungi, for example *Saccharomyces* or *Candida* spp.

In some embodiments, the dried viable cells may be cells of a live bacterial vaccine. Live bacterial vaccines are generally bacterial cells whose virulence has been attenuated, for example by the inactivation of one or more virulence genes. Many examples of attenuated bacterial cells suitable for use as vaccines are known in the art.

A bacterial vaccine may be an attenuated cell of a bacterial pathogen. The expression of native endogenous antigens of the pathogen by the attenuated vaccine may stimulate or prime a protective immune response against virulent non-vaccine strains of the pathogen. Suitable bacterial vaccines include attenuated cells of cells of *Vibrio cholerae*, Enterotoxic strains of *E. coli*, such as 0157:H7, 0121 and 0104:H21, *Shigella* species, such as *S. dysenteriae, S. sonnei, S. boydii* and *S. flexneri, Campylobacter* species such as *C. jejuni*, and *Salmonella* species, such as *Salmonella enterica* (especially, serovar Typhi).

Live bacterial vaccines for use in the therapeutic or prophylactic treatment of typhoid are well-known in the art and include *Salmonella typhi* strains Ty21a (Vivotif™), Ty800, CVD908, CVD908-htr, CVD915, and ZH9.

Live bacterial vaccines for use in the therapeutic or prophylactic treatment of cholera are also well known in the art and include JBK-70, CVD 101, CVD 102, CVD 104, CVD 105,395N1, JJM43, TCP2, CVD 103, CVD 103-RM, CVD 103-HgR (Mutachol®), CVD110, Bahrain-3, Peru-3, Peru-5 and Peru-15.

Live bacterial vaccines for use in the therapeutic or prophylactic treatment of shigellosis and bacterial dysentry are also well known in the art and include attenuated vaccine strains of attenuated *Shigella*, such as CVD 1204 and WRSS1.

Live bacterial vaccines for use in the therapeutic or prophylactic treatment of diarrhoea are also well known in the art and include attenuated enterotoxic *E. coli* cells, such as PTL002 and PTL003.

Live bacterial vaccines for use in the therapeutic or prophylactic treatment of listeriosis are also well known in the art and include attenuated strains of *Listeria monocytogenes*, such as Lmdd.

A bacterial vaccine may comprise heterologous nucleic acid which encodes an exogenous antigen i.e. an antigen not naturally expressed by the vaccine cell (for example a human or viral antigen or an antigen from different bacterial species). The bacterial vaccine may stimulate or prime a protective immune response against the exogenous antigen, for example when the antigen is displayed on the surface of a pathogen or a diseased cell, such as cancer cell or a virally infected cell.

The term "heterologous" indicates that a nucleic acid sequence is a recombinant sequence which has been introduced into a construct, vector or cell, artificially using genetic engineering or recombinant means, i.e. by human intervention. Nucleotide sequences which are heterologous do not occur together in nature. Nucleotide or amino acid sequences which are heterologous to a cell are non-naturally occurring in cells of that type, variety or species (i.e. exogenous or foreign). A nucleic acid sequence which is heterologous to a cell may encode a heterologous amino acid sequence i.e. an amino acid sequence which is exogenous or foreign to the cell.

In some embodiments, the heterologous nucleic acid may be expressed by the microbial cell to produce the exogenous antigen. The exogenous antigen may be secreted from the microbial cell, displayed on the surface of the microbial cell or remain intracellular within the microbial cell.

In other embodiments, the heterologous nucleic acid may not be expressed by the microbial cell. For example, the heterologous nucleic acid may be transferred to a host cell of the individual following delivery to the intestine and expressed in the host cell. The heterologous nucleic acid may be expressed to produce the exogenous antigen, for example in a method of DNA vaccination or DNA transfer, or may be expressed to produce a sense or anti-sense RNA molecule, for example in a method of RNA interference.

Suitable exogenous antigens which may be encoded by a heterologous nucleic acid include disease-related antigens such as tumour antigens and antigens of viral, bacterial and other pathogens, for example antigens derived from *Streptococcus mutans, Shigella sonnei, Escherichia coli, Campylobacter jejuni, Mycobacterium leprae, Mycobacterium tuberculosis, Vibrio cholerae, Yersinia pestis, Bacillus anthracis*, HIV, Influenza virus, hepatitis virus, papilloma virus *Plasmodium falciparum, Francisella tularensis*, and *Schistosoma mansoni*, or antigens derived from tumours such as Her2/neu or prostate specific antigen (PSA).

Other suitable exogenous antigens include molecules from the individual such as antibody idiotypes, for example for the generation of an anti-idiotypic immune response.

Optionally, the bacterial vaccine may also co-express a recombinant heterologous immunomodulatory polypeptide, for example a cytokine, such as TNF-alpha, GM-CSF, IL-1, IL-6, IL-12, IL-18, IFN-alpha, IFN-gamma, a chemokine such as CCL-25, or an antibody or antibody fragment or other binding polypeptide that inhibits cytokines (e.g. IL-10, TGF-beta) or other immune response mediators or immune cells (such as regulatory or suppressor T cells). This may be useful in increasing the immune response to the exogenous antigen.

Suitable bacterial vaccines for the expression of exogenous antigens include live bacterial vaccine strains, such as attenuated pathogenic bacteria, such as *Salmonella enteric, Vibrio cholerae, Enterotoxic E. coli, Shigella*, and *Campylobacter jejuni* and non-pathogenic bacterial cells, including enteric bacteria such as Enterobacteriaceae, and other bacteria such as *Bacillus subtlis* and lactic acid bacterial species, e.g. Lactococci spp such as *L. lactis* (Nature Reviews Microbiology (2008) 6:349).

The dried viable cells in the solid formulation may be a homogeneous population of the same type of cells (for example, cells of the same strain of micro-organism). Alternatively, the dried viable cells in the solid formulation may be a heterologous population containing a mixture of different types of cells. For example, the formulation may comprise cells of two or more, three or more, four or more, or five or more different types. Different types of cells may include cells of different strains or species of micro-organism and/or cells with different genetic modifications.

The formulations described herein may be administered to any suitable individual. For example, the individual may be a human or a non-human animal, such as a rodent (e.g. a guinea pig, a hamster, a rat, a mouse), murine (e.g. a mouse), canine (e.g. a dog), feline (e.g. a cat), equine (e.g. a horse), porcine (e.g. a pig), a primate, simian (e.g. a monkey or ape), a monkey (e.g. marmoset, baboon), an ape (e.g. gorilla, chimpanzee, orang-utan, gibbon), a bird (e.g. chicken), or a fish (e.g. salmon, trout).

For example, formulations as described herein comprising dried viable *salmonella* cells may be useful as vaccines in the veterinary treatment of non-human animals, such as pigs and horses.

Suitable individuals may be identified or selected as being in need of treatment.

The formulation preferably comprises a therapeutically-effective or prophylactically-effective amount of dried viable cells.

The terms "therapeutically-effective amount" or "prophylactically-effective amount" as used herein, pertains to that amount of a dried viable cells which is effective for producing some desired therapeutic or prophylactic effect, respectively, commensurate with a reasonable benefit/risk ratio.

A formulation described here may for example comprise $10^3$ or more, $10^4$ or more, $10^5$ or more, $10^6$ or more, $10^7$ or more, $10^8$ or more, $10^9$ or more, or $10^{10}$ or more dried viable cells.

Dried viable cells in the formulations described herein retain at least 0.1%, at least 1%, at least 5%, at least 10%, at least 20%, at least 40% or at least 60% viability following rehydration. A significant number of cells within the formulation are therefore capable of metabolic activity and cell division, following rehydration. Methods of assessing the viability of cells are well-known in the art and include, for example plate assays for colony forming units (CFU).

Preferably, the dried viable cells in the formulations described herein retain viability as set out above when the formulation is stored at room temperature for prolonged periods (e.g. 15° C. to 30° C. for 24 months or longer).

Dried cells have reduced moisture content relative to undried cells. For example, dried cells may contain 10% or less, 5% or less, 4% or less, 3% or less, or 1% or less residual moisture, relative to the same cells before drying.

Cells suitable for use as described herein may be dried by any convenient method which does not significantly affect cell viability.

A range of suitable methods are known in the art, including freeze-drying, ambient temperature drying, spray drying, fluidised bed drying, foam drying, directly drying during granulation for tabletting, and freezing with cryoprotectants (Potts (2004) Micro Rev 58:755-805; Crowe et al (1990) Cryobiol. 27:219-231; Lievense et al (1994) Adv Biochem Eng Biotechnol. 51 45-89). Optionally, drying may be carried out in the presence of a stabilising agent, for example a disaccharide, and/or a pharmaceutical excipient, for example, a polymer such as hydroxy propyl methyl cellulose.

In some embodiments, the cells may be lyophilised by freeze-drying. Freeze-drying involves the removal of water from a frozen material by sublimation and desorption at reduced pressure. Suitable freeze-drying techniques are well known in the art. (F. Franks European Journal of Pharmaceutics and Biopharmaceutics 1997 (45)221-229; Fundamentals of freeze-drying JD Mellor Academic Press 1978). Optionally, cells may be freeze-dried in the presence of a stabilising agent, for example a disaccharide such as trehalose (Israeli et al (1993) Cryobiol 30 519-523; Leslie et al (1995) Appl. Env. Microbiol. 61 3592-3597) and/or a pharmaceutical excipient or other components of the formulation.

In some embodiments, the cells may be subjected to disaccharide-stabilised drying. This may comprise increasing the intracellular level of a disaccharide, such as trehalose, in the cells and then drying the cells in the presence of a carbohydrate stabilising agent, for example, by evaporation and at reduced pressure and non-freezing temperatures. Suitable carbohydrate stabilising agents include disaccharides such as trehalose, maltitol, lactitol, palatinit, GPS (alpha-D-glucopyranosyl-1->6-sorbitol), GPM (alpha-D-glucopyranosyl-1->6-mannitol), maltooligosaccarides, and hydrogenated maltooligosaccarides. Suitable disaccharide-stabilised drying methods are well known in the art and are described, for example in Crowe J H et al Annu Rev Physiol 1998; 60:73-103. Bullifent H L, et al. Vaccine 2000 Dec. 8; 19(9-10):1239-45; Garcia De Castro A, et al Appl Environ Microbiol 2000 September; 66(9):4142-4; U.S. Pat. No. 6,468,782 and U.S. Pat. No. 6,610,531.

Bile acids are steroid acids which are produced in the liver by the oxidation of cholesterol and secreted into the intestine as components of bile. Bile acids include cholic acid, deoxycholic acid and chenodeoxycholic acid.

A bile acid binding agent or sequestrant is a compound which binds, absorbs or sequesters bile acids. Suitable bile binding agents include positively charged polymers which bind to the negatively charged carboxylic acid head group of bile acids. Positively charged polymers which bind to bile acids include anion-exchanging resins, such as cholestyramine (e.g. Questran™ or Dowex 1×2™), colestilan, colestimide, colextran hydrochloride, colesevelam HCl, colestipol, DEAE-dextran, aminated cellulose, DEAE-cellulose, TEAR-cellulose, Q-sepharose, QAE Sephadex, quaternised hydroxyethyl cellulose ethoxylate and aminated chitosan.

Suitable positively charged polymers are known in the art for use as cholesterol lowering agents, and are described, for example in U.S. Pat. No. 4,557,930, U.S. Pat. No. 3,308,020, U.S. Pat. No. 3,383,281, U.S. Pat. No. 3,499,960, U.S. Pat. No. 3,780,171, WO2005023305 and GB929,391.

Other suitable bile binding agents include hydrophobic polymers which bind to the hydrophobic cholesterol tail of bile acids. Suitable hydrophobic polymers include polystyrene-related polymers.

Other suitable agents may also include naturally occurring agents, such as dietary fibre, such as carob (Dongowski Food Chemistry 2007 104:p 390-397) or alfalfa (Kritchevsky and Story Journal of Nutrition 1974, 104(4):p 458-462), activated carbon, and bone char.

The bile binding agent may be in any shape or form within the formulation, for example granules, powders, beads, membranes or porous monoliths.

The data set out herein shows that a small amount of bile binding agent is sufficient to protect dried viable cells from bile acid toxicity. The amount of bile binding agent in a formulation described herein will generally be significantly less than the amount required to bind all the bile acids to which the formulation is exposed in the intestine of an individual.

A solid formulation may be in a unit dosage form and may comprise 5 g or less, 2 g or less, 1 g or less or 0.5 g or less of solid material.

A solid formulation as described herein may comprise less than 95% (w/w), less than 90% (w/w), less than 80% (w/w), less than 70% (w/w), less than 60% (w/w), less than 50% (w/w), less than 40% (w/w), less than 30% (w/w), less than 20% (w/w), less than 10% (w/w), less than 1% (w/w) or less than 0.1% (w/w) of said bile acid binding agent.

A solid formulation as described herein may comprise greater than 5% (w/w), greater than 10% (w/w), or greater than 20% (w/w), greater than 30% (w/w), greater than 40% (w/w), greater than 50% (w/w), greater than 60% (w/w), greater than 70% (w/w), greater than 80% (w/w), greater than 90% (w/w), or greater than 95% (w/w) of said bile acid binding agent.

The ratio by weight of cells to bile acid binding agent in the formulation may be 5 or less, 1 or less, 0.5 or less, 0.1 or less, 0.01 or less, 0.001 or less, or 0.0001 or less.

The ratio by weight of bile acid binding agent to cells in the formulation may be 0.2 or more, 1 or more, 10 or more, 100 or more, 1000 or more, or 10000 or more.

In some preferred embodiments, the dried viable cells, bile acid binding agent and other components of the formulation may be encapsulated in a polymeric shell.

The polymeric shell may be useful in further increasing the bile resistance of the formulation.

Preferably, the polymeric shell comprises an amphiphilic hydrophobic-hydrophilic polymer, such as hydroxypropyl methylcellulose (HPMC). Suitable polymeric shells are commercially available.

In some preferred embodiments, a solid formulation as described herein may be covered with an enteric coating.

An enteric coating is impermeable outer layer that protects the dried viable cells from acid damage as the formulation passes through the stomach and then allows the release of the cells when the formulation reaches the intestine. The use of enteric coatings is well-known in the art.

Enteric coatings may be pH sensitive. For example, an enteric coating may be non-labile under acidic conditions within the stomach (e.g. pH 1 to 3) but may be labile at higher pH within the intestine (e.g. pH above 5.5).

Suitable polymeric materials for use in enteric coatings are well known in the art and may, for example, include fatty acids, waxes, Shellac™, cellulose acetate phthalate (CAP), methacrylic acid copolymers, methyl acrylate-methacrylic acid co-polymers, cellulose acetate succinate, hydroxypropyl methylcellulose acetate succinate, hydroxylpropyl methyl cellulose phthalate, polyvinyl acetate phthalate (PVAP), cellulose acetate trimellitate, carboxymethyl ethylcellulose, and methyl methacrylate-methacrylic acid copolymers.

A solid formulation as described herein may further comprise one or more additional components, for example to modify or adjust the properties of the formulation for specific applications.

For example, a formulation may further comprise a delayed release agent which controls the release of the cells from the formulation into the intestine, after dissolution of the enteric coating, for example by forming a stable gelatinous layer that slowly erodes to release the cells.

Suitable delayed release agents include hydroxypropyl methylcellulose (HPMC), hydroxyethyl cellulose, other modified celluloses, natural gums such as guar gum, polyethylene oxide, polyvinyl alcohol, and poly (lactic-co-glycolic acid).

Dried viable cells may be sensitive to toxins in the intestine other than bile acids, for example lysozyme; antimicrobial peptides such as defensins; and digestive enzymes, such as pepsin, trypsin and lipase. A formulation may further comprise agents to protect the cells from such toxins. For example, a formulation may comprise a cation-exchanging resin to bind and protect dried viable cells from positively charged enzymes, such as lysozyme.

Suitable cation-exchanging resins include ion exchange resins such as Dowex 50 w×1 resin, sodium polystyrene sulfonate, or polymers such as carboxymethylcellulose or alginic acid.

A formulation may further comprise stabilisers to maintain the viability of the dried cells. Examples of suitable stabilisers include carbohydrates as described above.

A formulation may further comprise one or more pharmaceutically acceptable carriers, adjuvants, excipients, binders, disintegrants, bulk agents, glidants, diluents, fillers, buffers, stabilisers, preservatives, lubricants, or other materials well known to those skilled in the art and optionally other therapeutic or prophylactic agents. In some embodiments, a formulation may further comprise one or more mucoadhesives which hold the formulation in the intestine during release of the bacteria. Suitable mucoadhesives include polyvinyl pyrrolidone, polyacrylates, chitosan, methyl cellulose, carboxymethylcellulose, hydroxypropylcellulose and other cellulose derivatives.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington: The Science and Practice of Pharmacy, 21st edition, Mack Publishing Company, Easton, Pa., 2005; and Handbook of Pharmaceutical Excipients, 5th edition, 2006, Pharmaceutical Press, London.

In the production of the formulations described herein, the bile acid binding agent may be combined with the viable cells at any stage in the production process.

For example, a formulation may be produced by drying viable cells and then admixing the dried viable cells with a bile acid binding agent and optionally a pharmaceutically acceptable carrier and/or other materials described above. Alternatively, a formulation may be produced by admixing viable cells with the bile acid binding agent and optionally pharmaceutically acceptable carrier and/or other materials described above to produce an admixture and the admixture may then be dried.

Suitable methods of drying are described in more detail above.

The dried viable cells and bile acid binding agent may be admixed with further pharmaceutically acceptable carriers, adjuvants, excipients and/or other materials described above; compressed, moulded or otherwise made into a suitable formulation for oral delivery; and/or covered with an enteric coating to produce the formulation.

The resistance of the cells in the formulation to exposure to bile may be determined. The amount of cells and/or bile binding agent in the formulation may be altered to optimise the resistance of the cells to bile. For example, if reduced numbers of viable cells can be recovered from the formulation after bile exposure, relative to controls, then the amount of bile acid binding agent in the formulation may be increased.

Suitable solid formulations for oral administration may consist of one or more discrete units, such as tablets, pellets, pills or capsules. In some embodiments, a discrete unit such as a pill or capsule may comprise multiple small sub-units, such as granules or powders.

Solid formulations for oral administration may conveniently be presented in unit dosage form and may be prepared by any methods well known in the art. Such methods may include the step of bringing into association the dried viable cells and the bile acid binding agents with the carrier which constitutes one or more accessory ingredients.

In general, the formulations are prepared by uniformly and intimately bringing into association the admixture of dried viable cells and bile acid binding agents with finely divided solid carriers, and then if necessary shaping the product.

Formulations suitable for oral administration (e.g. by ingestion) may be presented as discrete units such as capsules, cachets or tablets, each containing a predetermined amount of the dried viable cells and the bile acid binding agent; for example as a powder or granules.

A tablet may be made by conventional means, e.g. compression, moulding, wet granulation or dry granulation, optionally with one or more accessory components, such as binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). For example, compressed tablets may be prepared by compressing in a suitable machine the active compound in a free-flowing form such as a powder or granules, optionally mixed with one or more accessory components. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose or other delayed release agents in varying proportions to provide the desired release profile. As described above, tablets, pellets, pills, capsules, and other solid formulations may optionally be provided with an enteric coating, to provide release in parts of the gut other than the stomach.

Capsules comprising dried cells and bile acid binding agent in a powder or granule form encapsulated by a polymeric shell may be made by conventional means.

The components may be disposed in various different arrangements within the formulations described herein and the precise arrangement of the components will depend on the specific properties which are required for a given application. For example, a formulation may be homogenous i.e. the dried viable cells and bile binding agents may be distributed homogenously within the formulation, or it may be heterogeneous i.e. the dried viable cells and bile binding agents may be distributed heterogeneously within the formulation.

Figure 6:
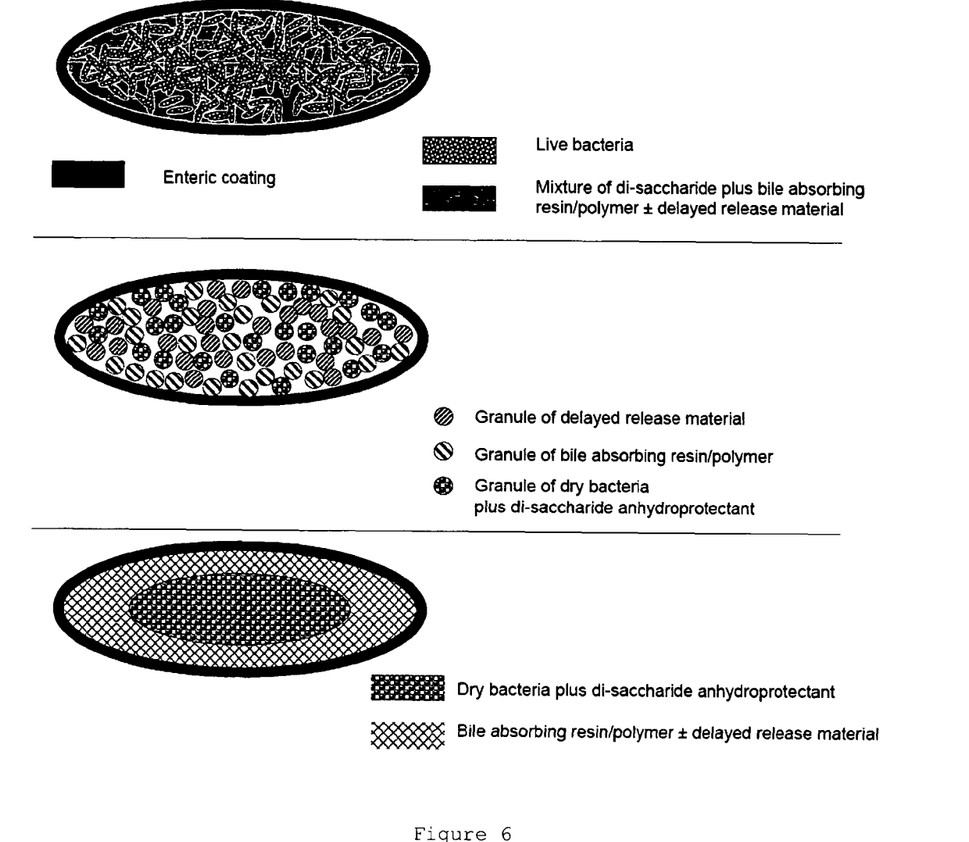
FIG. 6 shows three examples of possible formulations for oral dosage forms.

Examples of different arrangements of components in the formulations described herein are shown in FIG. 6.

In some embodiments, a formulation may comprise; a core which comprises live dried bacteria and bile binding agent, and; a coating, preferably an enteric coating, which surrounds the core. Optionally, the coating may be a polymeric shell which encapsulates the core.

Alternatively, a formulation may comprise a core of pharmaceutically acceptable excipient which comprises granules of dried viable bacteria and granules of dry bile binding agent. Optionally, the core may further comprise granules of delayed release material. Optionally, the core may be encapsulated in a polymeric shell. Optionally, the formulation may further comprise an enteric coating which surrounds the core.

Alternatively, a formulation may comprise a core of viable dried bacteria which is surrounded by a layer of bile binding agent. Optionally, the layer of bile binding agent may further comprise a delayed release material. Optionally, the core and the layer of bile binding agent may be encapsulated in a polymeric shell. Optionally, the formulation may further comprise an enteric coating which surrounds the layer of bile binding agent.

Formulations as described herein are stable at room-temperature i.e. cells remain viable after prolonged storage at room-temperature (e.g. 15° C. to 30° C.)

Combinations of a bile acid binding agent and dried viable cells, e.g. in a formulation as described above, are useful in delivering live cells to the intestine of an individual.

Formulations as described herein may be useful for medicinal, therapeutic or prophylactic applications. For example, a combination of a bile acid binding agent and dried viable cells, e.g. in formulation as described above, may be useful in the therapeutic or prophylactic treatment of the human or animal body.

The term "therapeutic treatment" as used herein in the context of treating an individual for a condition, pertains generally to treatment and therapy, whether of a human or a non-human animal (e.g. in veterinary applications), in which some desired therapeutic effect is achieved, for example, the inhibition of the progress of the condition, and includes a reduction in the rate of progress, a halt in the rate of progress, amelioration of the condition or one or more symptoms thereof, and cure of the condition.

The term "prophylactic treatment" as used herein in the context of a treating an individual for a condition, pertains generally to treatment which prevents or reduces the risk of the occurrence or recurrence of the condition or one or more symptoms thereof. Prophylactic treatment may, for example, be carried out on an individual (e.g. a human or a non-human animal) who is not at the time of treatment suffering from the condition or who does not display symptoms of the condition.

In particular, a combination of a bile acid binding agent and dried viable cells, e.g. in formulation as described above, may be useful in the therapeutic or prophylactic treatment of pathogen infection in an individual. A method of treating a pathogen infection in an individual may comprise orally administering a combination of a bile acid binding agent and dried viable cells, e.g. in formulation as described above, to an individual in need thereof.

Pathogen infections include bacterial infections, such as cholera (*V. cholerae*), typhoid (*S. typhi*), dysentery (*Shigella* spp), anthrax (*Bacillus anthracis*), plague (*Yersinia pestis*), tuberculosis (*Mycobacterium tuberculosis*), leprosy (*Mycobacterium leprae*), campylobacteriosis (*Campylobacter* spp) and gastroenteritis (enterotoxic *E. coli* and *Salmonella* spp); viral infections such as influenza, HIV-AIDS, smallpox and SARS, and parasitic infections such as malaria (*Plasmodium* spp), schistosomiasis (*Schistosoma* spp).

A combination of a bile acid binding agent and dried viable cells, e.g. in a formulation as described above, may also be useful in methods of immunisation and/or immunotherapy, for example by stimulating or priming an immune response to a disease-related antigen which is encoded and preferably expressed by the cells. A method of treating an individual by immunisation or immunotherapy may comprise orally administering a combination of a bile acid binding agent and dried viable cells, e.g. in formulation as described above, to an individual in need thereof.

As described above, the disease-related antigen may be naturally expressed by the cells (e.g. in an attenuated bacterial vaccine) or the disease-related antigen may be an exogenous antigen which is expressed in the cell from heterologous nucleic acid.

The cells may further comprise heterologous nucleic acid encoding the an immunomodulatory polypeptide, for example a cytokine such as TNF-alpha, GM-CSF, IL-1, IL-6, IL-12, IFN-alpha or IFN-gamma; a chemokine such as CCL-25, or an antibody or other binding molecule which inhibit cytokines (e.g. IL-10, TGF-beta) or other immune response mediators or cells (such as regulatory or suppressor T cells), leading to enhanced immune responses.

Disease-related antigens include tumour antigens and antigens of viral, bacterial and other pathogens as described above. For example, the cells may express an antigen from a pathogen such as *Streptococcus mutans, Shigella sonnei, Campylobacter jejuni, Escherichia coli, Mycobacterium leprae, Mycobacterium tuberculosis, Vibrio cholerae, Yersinia pestis, Bacillus anthracis*, HIV, Influenza virus, hepatitis virus, *Plasmodium falciparum, Francisella tularensis*, or *Schistosoma mansoni*, or an antigen from a tumour, such as Her2/neu or prostate specific antigen (PSA) in order to elicit or prime an immune response to the pathogen or tumour. Formulations as described herein may thus be useful in the therapeutic and prophylactic treatment of pathogen infection and cancer.

A combination of a bile acid binding agent and dried viable cells, e.g. in a formulation as described above, may also be useful in delivering viable cells to the intestine, for example to restore the microbial flora of the intestine in an individual. This may be useful, for example, following treatment with antibiotics. A method of restoring the microbial flora of the intestine may comprise orally administering a combination of a bile acid binding agent and dried viable cells, e.g. in formulation as described above, to an individual in need thereof e.g. following treatment with antibiotics.

A combination of a bile acid binding agent and dried viable cells, e.g. in a formulation as described above, may also be useful in the therapeutic and prophylactic treatment of inflammatory intestinal disease or one or more symptoms thereof in an individual. A method of treating inflammatory intestinal disease or one or more symptoms thereof may comprise orally administering a combination of a bile acid binding agent and dried viable cells, e.g. in formulation as described above, to an individual in need thereof.

A combination of a bile acid binding agent and dried viable cells, e.g. in a formulation as described above, may also be useful in the therapeutic and prophylactic treatment of renal stone formation in an individual. A method of treating renal stone formation may comprise orally administering a combination of a bile acid binding agent and dried viable cells, e.g. in formulation as described above, to an individual in need thereof.

A combination of a bile acid binding agent and dried viable cells, e.g. in a formulation as described above, may also be useful in reducing cholesterol levels in an individual. A method of reducing cholesterol levels may comprise orally administering a combination of a bile acid binding agent and dried viable cells, e.g. in formulation as described above, to an individual in need thereof.

A bile acid binding agent and viable dried cells may be used in the manufacture of a medicament for use in any of the therapeutic and prophylactic applications and treatments described above.

Suitable formulations, bile acid binding agents and viable dried bacterial cells are described in more detail above.

The methods described herein may be useful, for example, in improving the efficacy of a therapeutic agent which comprises dried viable cells, such as a bacterial vaccine. A method of improving the efficacy of such an agent may comprise formulating the agent with a bile acid binding agent, as described herein.

The methods described herein may also be useful, for example, in increasing the survival of dried viable cells in the intestine of an individual. A method of increasing the survival of dried viable bacteria cells in the intestine may comprise formulating the cells with a bile acid binding agent, as described herein.

Another aspect of the invention provides the use of a bile acid binding agent as described herein in a method described herein, for example, a method of producing a solid formulation comprising dried viable cells for oral administration; increasing the survival of dried viable bacteria cells in the intestine of an individual or improving the efficacy of a therapeutic agent which comprises dried viable cells.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described below.

EXPERIMENTS

We used the live bacterial vaccine strain SLDAPD pUC18I as a model for oral bacterial delivery [13]. Bacteria were grown overnight in M9 medium (with essential amino acids and nutrients) plus 250 mM NaCl, then 10 microliter samples were dried in phosphate buffered saline (PBS) plus 40% trehalose and 1.5% PVP in a desiccator, as described ([14]). Replicate samples were kept dry or rehydrated with 200 microliters PBS or water and left for 1, 5 or 20 minutes as indicated. Dry or recovered samples or control cells from rich broth cultures were then tested by incubation for 1 h diluted extensively in acid or bile solution or control buffer, as indicated, followed by dilution, plating on agar plates, and counting overnight colonies. Bacterial counts were corrected for the dilution during recovery and testing, and expressed as cfu/ml relative to the original 10 µl sample volume.

Figure 1:
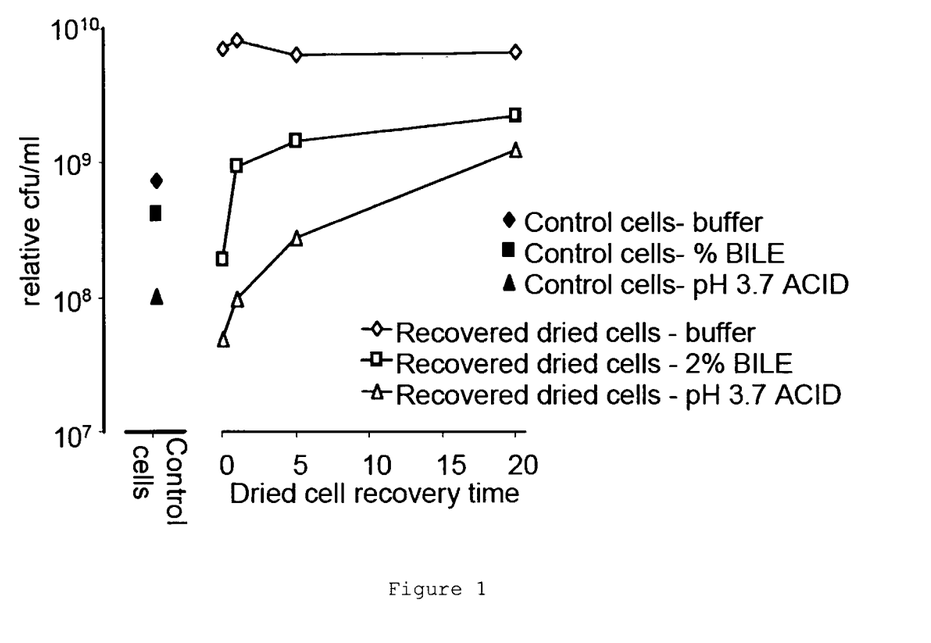
FIG. 1 shows the rapid recovery of bile tolerance after rehydration.

Dried bacteria were found to recover bile tolerance very rapidly when rehydrated in water or buffer prior to exposure to bile. A dried preparation of bacteria that lost 50× viability when rehydrated in bile, gained 5× better survival within 5 minutes of rehydration, and 20× better survival after 20 minutes (FIG. 1).

Similar results were obtained by rehydration in buffer and water. By 1 h after rehydration, bacteria behaved indistinguishably from control cells from liquid cultures.

The live bacterial vaccine strain SLDAPD pUC18I [13] and *E. coli* strain K12 DH5a (Invitrogen) were grown overnight in M9 medium plus 250 mM NaCl then 10 µl samples were dried in PBS/40% trehalose/1.5% PVP in a desiccator, as described [12]. A 5% w/v solution of bile (Sigma, Ox-bile) in PBS was mixed with or without 10% w/v of cholestyramine (Dowex 1×2, Sigma, Poole UK) for 1 hour at room temperature. The cholestyramine was removed by centrifugation followed by filtration (0.2 micron, millipore). Measurement of bile salts using an enzymatic assay (Randox Total Bile Acid Assay, Randox labs, Co. Antrim) demonstrated that the concentration of bile salts was reduced from 130 mM to 0.8 mM by cholestyramine treatment. The resulting solutions were added to replicate samples of dried bacteria and cultured for 1 h, followed by dilution, plating, counting overnight colonies and calculation of relative cfu/ml.

Figure 2:
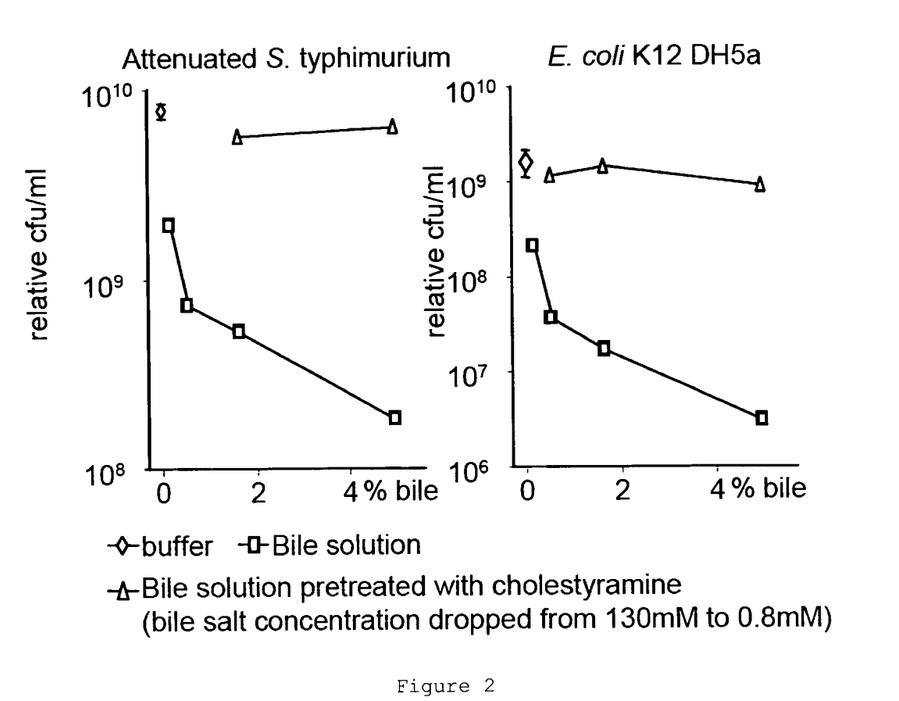
FIG. 2 shows that removing bile acids from bile solutions using BAR prevents the toxicity of bile solutions to dry bacteria.

Removal of bile acids by BAR was found to effectively prevent toxicity of bile solutions to dried bacteria (FIG. 2). FIG. 2 also demonstrates high bile toxicity to dried samples of a different strain of bacteria, *E. coli* K12, and shows that pre-treatment with cholestyramine protects these dried cells too.

10 µl dried samples of SLDAPD pUC18I (containing the ampicillin resistance gene) were dried in 6 ml test tubes. To replicate samples, either nothing or 150 mg of cholestyramine were added on top of the dried cells. Then, 2 ml of a 2% solution of bile in PBS or control PBS were added onto the cholestyramine, followed by incubation for 1 h at 37 degrees. After incubation, samples were taken, diluted, plated, and overnight colonies were counted on agar plates with or without ampicillin and relative cfu/ml calculated. Cholestyramine was sterilised prior to adding to bacterial samples by pretreatment with 70% Ethanol and extensive drying. Furthermore, the same number of colonies were found with or without ampicillin, indicating that only the test strain of bacteria were present and no contamination had occurred.

Figure 3:
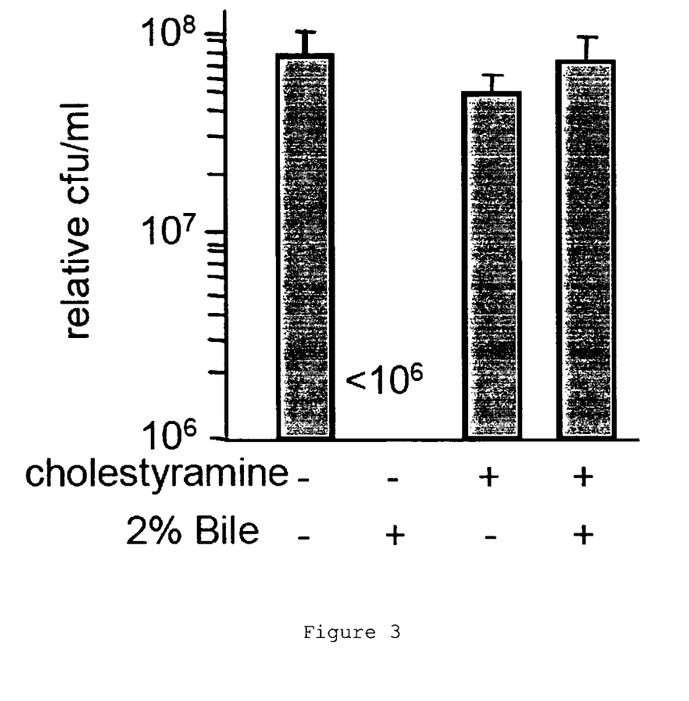
FIG. 3 shows that cholestyramine prevents bile toxicity.

The addition of BAR on top of dried bacteria followed by bile solution addition was found to block the toxicity of the bile solution. This demonstrates that sequential removal of bile followed by administration of bile acid-cleared liquid to dry bacteria is not required to protect bacteria, and demonstrates that bile acids complexed to BAR have no toxicity to dried bacteria (FIG. 3).

Figure 4:
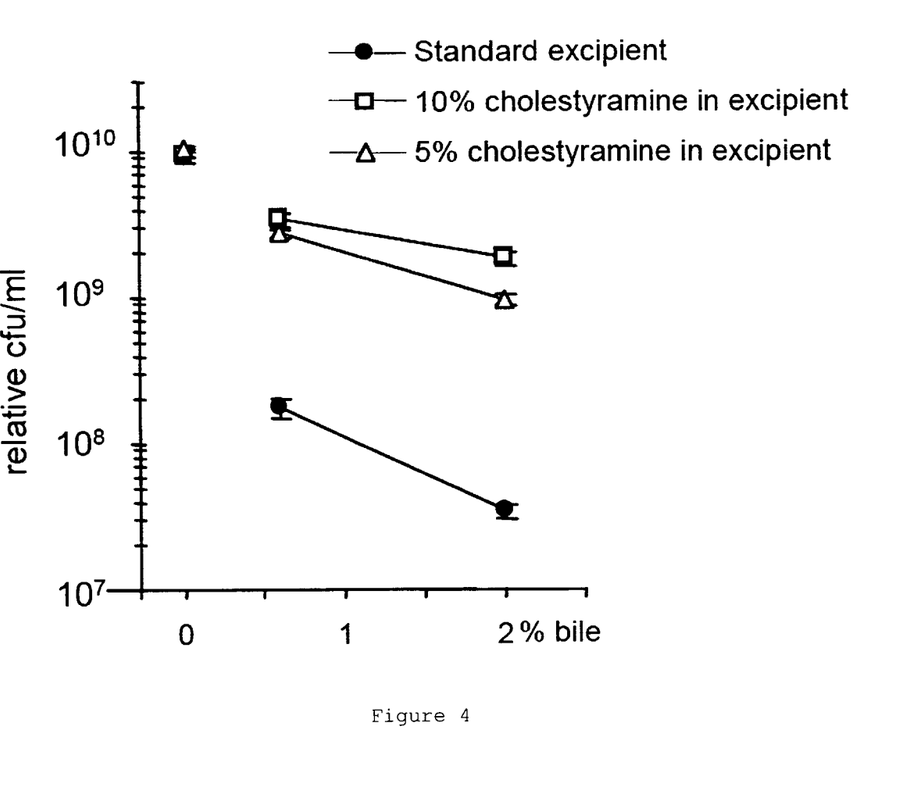
FIG. 4 shows that adding BAR to drying excipient prior to drying bacteria provides significant protection against toxicity when dried cells are resuspended in bile solutions.

Replicate 10 µl samples of SLDAPD pUC18I were suspended in either control excipient (40% trehalose, 1.5% PVP in PBS) or BAR-containing excipient (40% trehalose, 1.5% PVP plus 5 or 10% cholestyramine in PBS) and dried in 6 ml test tubes. To replicate samples, 2 ml of 2% or 0.4% bile solutions or control buffer were added and the tubes were incubated for 1 h at 37 degrees, followed by sampling, dilution and plating on agar plates. Inclusion of BAR in the drying excipient was found to provide effective protection of dried bacteria from bile, even at quantities unable to bind the total amount of bile acid present in a test solution (FIG. 4).

Crucially, simply drying bacteria with small quantities of cholestyramine added to the drying excipient was found to provide significant protection in conditions where no protection would be expected if the BAR was simply binding and sequestering bile acids. In FIG. 4, the amount of cholestyramine present is far smaller than the total amount of bile acids present in the test medium. Cholestyramine has a capacity of 1.2 mg bile salts per 1 mg (typical value, exact value depends on which bile acid is bound, [14]). Therefore, in the 10 µl dried bacteria sample there is 1 mg cholestyramine with a capacity for 1.2 mg bile acids, yet in the 2 ml 2% bile solution a total of 20 mg bile acids are present (typically the ox-bile used contains in excess of 50% bile acids by weight), greater than 15-fold excess of bile acids.

SLDAPD pUC18I cells were dried in standard excipient (40% trehalose, 1.5% PVP in PBS), then ground in a mortar to make a powder. The powdered dried bacteria were mixed in carefully weighed proportions as follows:

Control tablets—sucrose filler: 9% powdered dried bacteria/91% sucrose powder

Control tablets—MCC filler: 8% powdered dried bacteria/92% microcrystalline cellulose (MCC, Avicel PH101)

BAR tablets—Cholestyramine: 8% powdered dried bacteria/33% cholestyramine/58% MCC filler BAR tablets—Dowex 1×2: 6% powdered dried bacteria/63% Dowex 1×2 400 mesh resin/32% MCC filler 70-90 mg samples of the mixed powders were then pressed in a 7 mm die in a press (Port-A-Press from International Crystal Laboratories, supplied by Crystan Ltd, using 10 newton meters torque) to make compressed matrix tablets approximately 1 mm thick. The tablets were then tested in simulated intestinal conditions as follows: The tablets were weighed and individually added to 17 ml portions of International Pharmacopoeia simulated intestinal fluid, i.e. sodium/potassium phosphate buffer pH7.0 either alone or plus 1% ox bile solution, and incubated for 45 minutes at 37° C. Samples were taken, diluted, plated overnight, and live cfu counted. The bacterial count recovered was expressed in terms of the original dried bacteria weight, i.e. in cfu/mg of dried bacteria, and each bar represents a single tablet, with the error bar representing multiple bacterial counts for this tablet.

Figure 5:
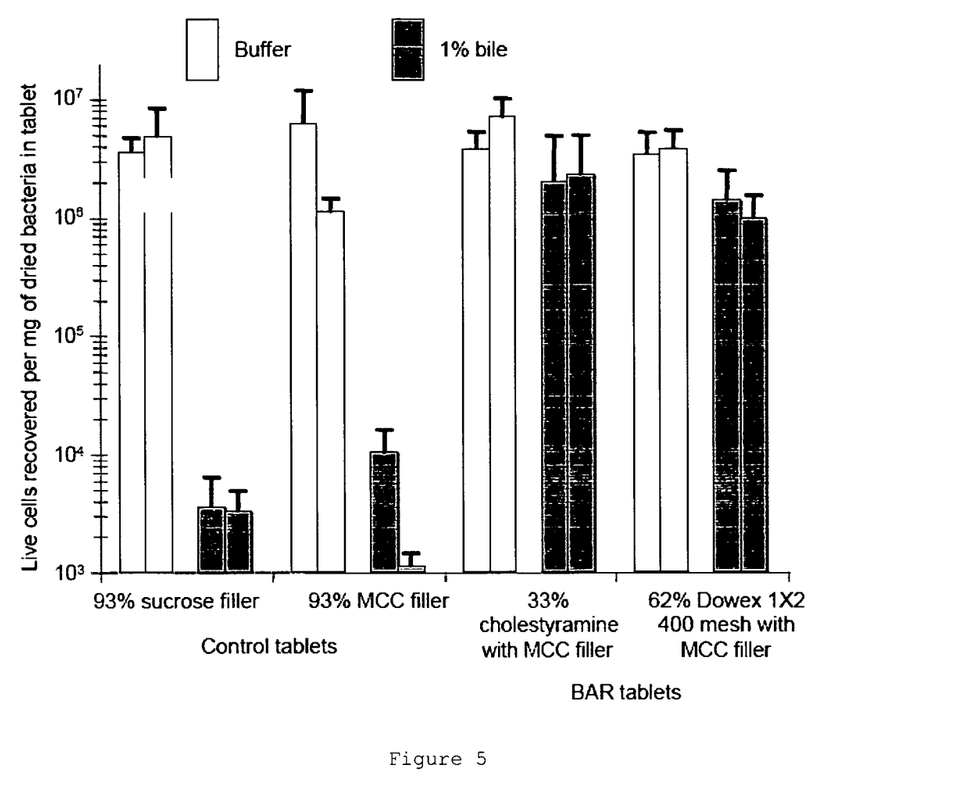
FIG. 5 shows that adding BAR to compressed matrix tablets provides significant protection against toxicity of a 1% bile solution

Prototype human tablets containing BAR plus dried bacteria were found to offer significant bile protection in a simulated intestinal release model (FIG. 5). We tested tablets containing live dried bacteria with or without addition of the BAR cholestyramine, or the equivalent ion exchange resin Dowex 1×2, by dissolution in buffer vs bile solutions. With control tablets containing dried bacteria diluted in sucrose as a filler, 1228-fold fewer cells were recovered after dissolution in 1% bile solution compared to dissolution in buffer alone, indicating significant bile toxicity. Similarly, tablets made using MCC as a filler, 638-fold fewer cells were recovered after dissolution in a 1% bile solution compared to buffer alone. In contrast, with tablets containing cholestyramine or Dowex 1×2 resin in addition to the dried bacteria and MCC filler, dissolution in bile only gave a 2.5 to 3.1-fold reduction in live cell recovery. This represents an improvement of 208 to 254-fold more live cells with the BAR tablet compared to control tablets. Importantly, the cholestyramine tablets contain a maximum of 24 mg cholestyramine having the capacity to bind a maximum of 29 mg bile acids but 17 ml of 1% bile solution contains approximately 85 mg bile acids, therefore the cholestyramine is not simply sequestering the total bile acids which are in excess in the test solution.

Without being bound in any way by theory, the formulation may work as follows: the cholestyramine in the excipient binds the bile acids present in the limited volume of buffer which is absorbed into the dry sample, and thus the dried bacteria are rehydrated in 'cleaned' water, allowing rapid recovery, as shown in FIG. 1. Subsequently, when the rehydrated sample disintegrates and disperses into the bile solution, the bacteria have already recovered significant bile resistance.

Even with the simple experimental formulation consisting of BAR added to the drying excipient, 50-fold more live bacteria were recovered with the BAR formulation (10% cholestyramine) than the control formulation when resuspended in a 2% bile solution, representing a significant improvement. This represents a 5-fold reduction in live cell recovery with the formulation when resuspended in 2% bile, as compared to 270-fold reduction in live cell recovery with the conventional control formulation with conventional drying excipient. Similarly, with the compressed matrix tablet formulation consisting of BAR mixed with dried bacteria prior to tablet compression, 208 to 254-fold more live bacteria were recovered with the BAR containing tablet formulation than with the control formulation when resuspended in a 2% bile solution, representing a significant improvement. This represents a 2.5 to 3.1-fold reduction in live cell recovery when dissolution in 1% bile, as compared to 1228 to 638-fold reduction in live cell recovery with the conventional control tablet formulation.

The ability of an optimal formulation to protect a dried live bacterial vaccine from bile was tested.

In these experiments, the mouse plague vaccine strain SL3261/pAHL was used [17]; similar results were obtained using the antibiotic-free plasmid maintenance strain SLDAPD/pUC18I [12, 16, 13]. Bacteria were counted using LB agar plates containing either ampicillin for SLDAPD/pUC18I or kanamycin for SL3261/pAHL to ensure only vaccine bacteria were counted. Bacteria were grown and dried as described in [12,16], and then several replicate dried preparations were pooled and ground to a homogeneous powder in a mortar and mixed with dry MCC to make a free-flowing powder for formulation and filling into capsules. This powder typically contained $2-5 \times 10^6$ cfu/mg and was stored in a vacuum desiccator at room temperature until testing; the preparation showed less than 10% loss of viability over a 2 month period.

This powder was mixed with MCC filler plus BAR at 25%, then either weighed directly into test tubes, or filled into size 00 capsules of the indicated shell material and weighed into test tubes. Between 20-30 mg bacteria were added per 1 g total powder, to ensure that 6-10 mg powdered dried bacteria were included per capsule. The mixed powder was manually filled into size 00 capsules of the indicated shell material using a Cap-M-Quick (Value Healthcare Company, Sheffield UK); a 6.4 mm diameter steel ball bearing was added to the capsule to sink it during dissolution.

Figure 7:
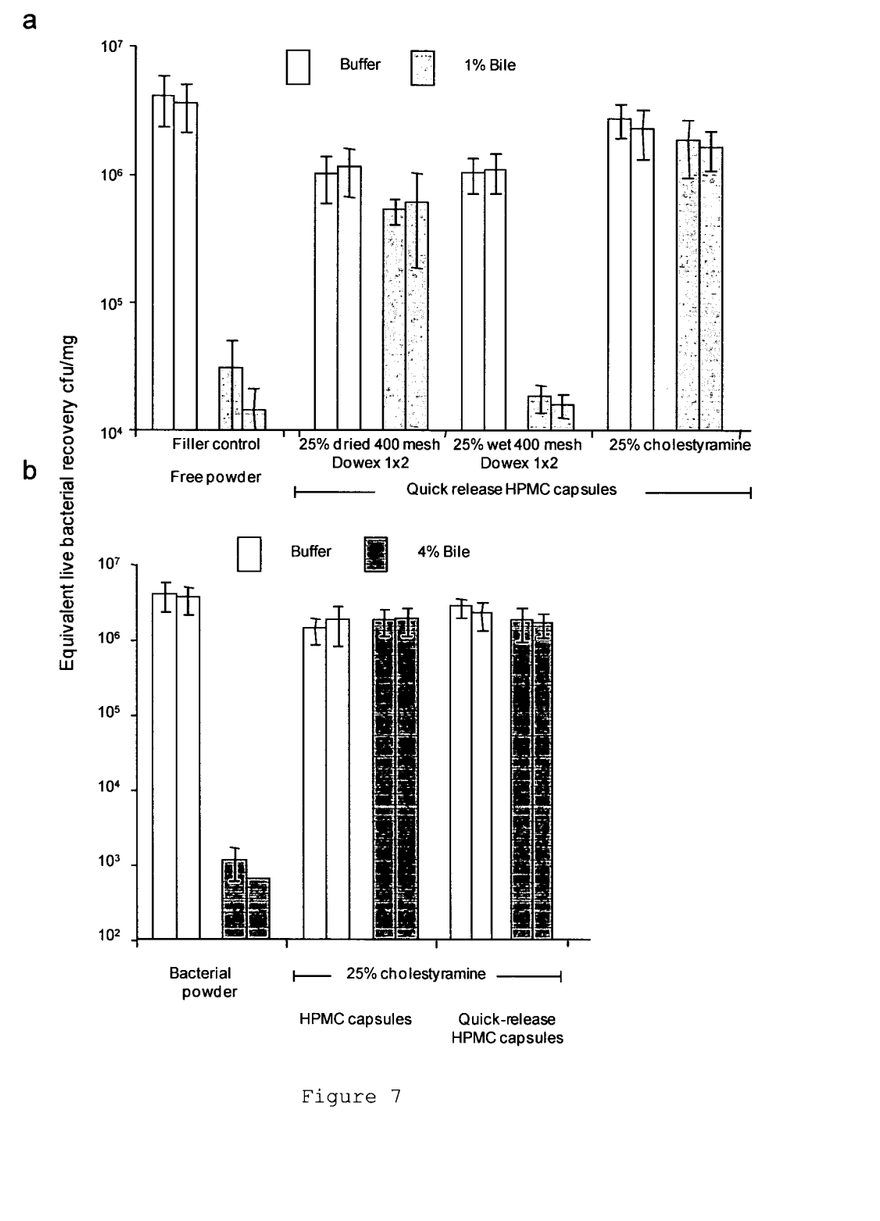
FIG. 7 shows the validation of optimised formulation for protecting cells of a dried live bacterial vaccine from bile

25 ml of buffer or 1% or 4% ox bile were added and incubated at 37° C. for 50 minutes, then the tubes were mixed thoroughly and samples taken, diluted, plated on agar plates with kanamycin, and incubated overnight. Colonies were counted and used to determine live cell number, expressed as CFU per mg of the initial dried vaccine powder. Dried stabilised cells of the mouse plague vaccine strain SL3261/pAHL were employed; similar protection was seen in separate experiments using dried cells of the vaccine strain SLDAPD/pUC18I.

The effect of differing BAR types on bile protection was studies within the Quick-release HPMC capsule shell. Quick-release HPMC capsules are modified HPMC capsules designed to give far faster release compared to conventional HPMC capsules. Imaging studies predicted that protection given by 400 mesh Dowex 1×2 could be significantly improved simply by removing moisture to generate a free-flowing non-aggregated powder, and indeed when dried 400 mesh Dowex 1×2 was added at 25% to dried LBV and MCC filler an impressive difference was seen, with dried 400 mesh Dowex 1×2 providing 92-fold protection compared to powder without capsules. In contrast the wet preparation of 400 mesh Dowex 1×2 gave no significant protection (FIG. 7*a*). Furthermore, cholestyramine gave even better protection than the dried 400 mesh Dowex 1×2, with 120-fold protection compared to powder without capsules, and showing no significant loss of bacteria in 1% bile compared to buffer (FIG. 7*a*).

Next, we made and tested an optimised formulation in an increased bile concentration. This formulation incorporated the protective features predicted by imaging and theoretical work—25% cholestyramine, an increased dose size and capsule geometry—and was also tested using conventional HPMC capsules Adding 25% cholestyramine BAR resulted in 100% recovery of viable cells in HPMC capsules under 4% bile conditions, with no difference in cell recovery between bile and buffer (FIG. 7*b*). Furthermore no significant loss of bacteria was detected in 4% bile compared to buffer when Quick-release HPMC capsules were also filled with 25% cholestyramine and dried LBV (FIG. 7*b*). Therefore simply adding 25% cholestyramine into dried LBV preparations can provide 4200-fold protection from 4% bile. The composition of pig bile is closer to that of humans [8], and a similar high degree of protection from pig bile at 1%, 4% and 8% was also observed, confirming that this optimised formulation can protect dried vaccine bacteria from excess concentrations of bile acids.

The inclusion of BAR in tablets provides protection from a solution of bile that contains a quantity of bile acids that far exceeds the maximal capacity of the BAR within the tablet [16]. Similarly, in the capsule experiments, the total amount of cholestyramine was 75 mg (25% of 300 mg powder), which can bind a maximum of 218-292 μmole bile acids [4]. This was added to 25 ml of a 4% bile solution that contained a total of 2500 μmole bile acids, representing an 8-11 fold excess of bile acids over BAR capacity, indicating that as with tablets, capsules containing BAR provide temporary protection whilst dry bacteria recover bile tolerance, rather than simply sequestering all bile acids within the test sample.

The ability of an enteric coated capsule and the BAR cholestyramine to protect dried live *Salmonella* vaccine from acid and bile was tested.

SL3261/pAHL bacteria were grown and dried in the same manner as previous experiments. Powdered dried bacteria were mixed with microcrystalline cellulose and cholestyramine in the ratio of 1:75:25 cells:MCC: cholestyramine. This powder was filled into size 00 standard HPMC capsules, approximately 300 mg per capsule, with a ball bearing to sink during dissolution testing. The capsules were either uncoated or dipped twice from each side into a 10% w/v solution of enteric polymer methacrylic acid:ethyl acrylate copolymer (Kollicoat MAE 100 P, BASF, Mannheim Germany) dissolved in a 3:2 v/v mix of methanol and dichloromethane, then dried overnight.

5 enteric coated capsules were individually immersed for 40 minutes in 20 ml 0.1 M HCl at 37° C. to simulate gastric acid in the stomach; as expected the enteric coating prevented dissolution or penetration of the capsule shell by the acid. These 5 capsules were then transferred into 2% ox bile dissolved in phosphate buffer pH 7.0. At the same time 2 coated and 3 uncoated capsules were individually added to 20 ml phosphate buffer pH7.0 (buffer); at the same time 2 uncoated capsules were added individually to 20 ml 0.1 M HCl. All capsules were then incubated at 37° C. for 1 h, then mixed thoroughly. The uncoated capsules completely dissolved in the acid within 1 h. After a further 1 h (2 h total incubation), samples were taken, diluted, and plated on agar plates containing kanamycin then incubated overnight. Colonies were counted and the live cell recovery calculated and expressed as colony forming units per ml; each bar represents 1 capsule and the error bars indicate 1 standard deviation.

Figure 8:
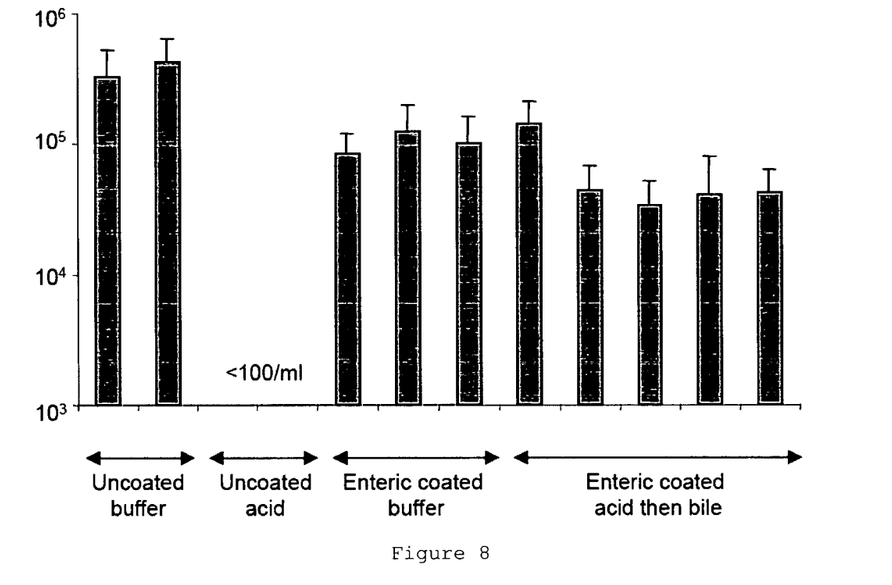
FIG. 8 shows the protection of a dried live *Salmonella* vaccine from acid and bile using an enteric coated capsule and the BAR cholestyramine.

Uncoated capsules were found to release high numbers of viable cells into the buffer, but no live cells were recovered in acid. In contrast, similar numbers of viable cells were recovered into buffer and into bile after acid immersion with the enteric coated capsules (see FIG. 8). This demonstrates that an enteric-coated solid dose containing the BAR cholestyramine protects cells of a live dried heterologous antigen bacterial vaccine from gastric acid followed by intestinal bile.

The ability of capsules containing the BAR cholestyramine to protect dried lactic acid bacteria from bile solutions was tested. Live lactic acid bacteria were commercially manufactured in powder form through a fermentation process and freeze drying. The culture was tested for *salmonella* and other pathogens by the manufacturer and supplied as a food supplement that is suitable for human consumption.

The dried lactic acid bacterial powder containing *Lactobacillus caseii* was mixed with microcrystalline cellulose (MCC) filler either with or without 50% w/w of the BAR cholestyramine, and then filled into HPMC capsules containing a 1 g ball bearing to sink the capsules. 13-15% w/w of capsule content was bacteria which correlates to 39-45 mg of a 300 mg capsule i.e. in the range $9.8 \times 10^9$-$11 \times 10^9$ CFU/capsule. Individual capsules were added to 50 ml tubes containing 25 ml of either control phosphate buffer pH7.0, or the indicated concentrations of ox bile and porcine bile in phosphate buffer for 1 h at 37° C. Samples were taken, diluted and portions plated on agar culture plates, incubated for 72 h at 37° C. after which colonies were counted and colony forming units (CFU) were calculated to indicate the number of live cells relative to the original weight of dried lactic acid powder added to the capsules. Each bar represents the mean of 4 individually tested capsules.

Figure 9:
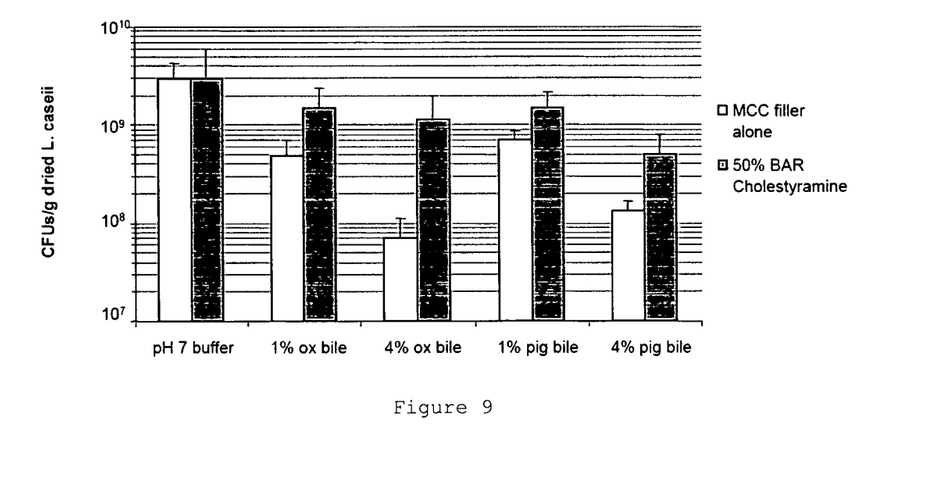
FIG. 9 shows the protection of a dried lactic acid bacteria from bile solutions in capsules using the BAR cholestyramine.

When dispersed in control buffer, the control capsules containing cells mixed with MCC filler alone were found to release the expected high numbers of live *L. caseii* cells; in contrast, increasing doses of bile gave reductions in live cell recovery, with 4% ox-bile giving over 30-fold killing. When cholestyramine was added into the capsule mixed with the bacteria and filler powders, less than 3-fold loss was seen with 4% ox-bile, giving over 10-fold protection against this high dose of bile. Similar results were seen with pig bile (FIG. 9). This demonstrates that a commercial, freeze-dried, food grade preparation of lactic acid bacteria may be protected from bile using the BAR cholestyramine.

The experimental data set out above shows that bile sensitive dried bacteria rapidly recover tolerance to bile, if rehydrated prior to bile exposure and pre-treatment of bile solutions with a bile acid sequestrant prevents bile toxicity to dried bacteria. Furthermore, adding the bile acid sequestrant on top of dried bacteria is shown to prevent bile toxicity and adding the bile acid sequestrant to the excipient prior to drying also provides significant protection against bile toxicity compared to bacteria dried in the conventional excipient. Matrix tablets and capsules containing the bile acid sequestrant also show increased viable bacteria release when added to bile solutions, compared to control tablets or capsules without the bile acid sequestrant.

After rehydration without bile acids, dried bacteria were found to recover bile resistance very rapidly. This demonstrates that dried bacteria may be allowed to recover in an oral delivery form in the intestine through rehydration with bile protection.

BAR are used conventionally to sequester bile acids and block reabsorbtion, but have not been previously shown to modulate the effect of bile acids in the intestine.

The data set out above also shows that if dry bacteria and bile acid binding agents are present together, that the toxicity of bile acids is blocked—i.e. the bile acids cannot kill the dried bacteria in the presence of bile acid binding agents. This shows that dried bacteria may be protected in vivo from the toxicity of bile acids.

The data set out above also show that if bacteria are dried in the presence of bile acid binding agents, then sufficient protection from bile toxicity is provided even in a situation where the total quantity of bile acid in the test tube is in great excess of the total capacity of the bile acid binding agents present in the dried bacterial formulation.

Bile acid sequestrants may therefore be incorporated into dose formulations to increase the efficacy of delivery of live bacteria to the intestine. When released into the intestine by a conventional enteric delivery system, the bile acid sequestrant will protect the dried bacteria from bile acids giving the bacteria time to rehydrate without bile acid toxicity, thereby allowing recovery of bile tolerance and improving live bacterial delivery to the intestine. For example, a bacterial vaccine (strain SL3261/pAHL) containing a recombinant antigen (plague F1 antigen in a plasmid) and a commercial dried preparation of the lactic acid bacterium *Lactococcus caseii* are protected from bile by the formulations described herein. Furthermore, the presence of an enteric coating as well as a bile acid sequestrant protects dose formulations from sequential exposure to acid followed by bile solutions (simulated ingestion).

REFERENCES

[1] Bergogne-Berezin E. Int J Antimicrob Agents 2000 December; 16(4):521-6.

[2] Bohm S K, Kruis W. Ann N Y Acad Sci 2006 August; 1072:339-50.
[3] Huyghebaert N et al Eur J Pharm Biopharm 2005 August; 60(3):349-59.
[4] Levine M M. Vaccine 2006 May 1; 24(18):3865-73.
[5] Prakash S et al Appl Biochem Biotechnol 2006 January; 128(1):1-22.
[6] Crowe J H, et al Annu Rev Physiol 1998; 60:73-103.
[7] Bullifent H L et al. Vaccine 2000 Dec. 8; 19(9-10):1239-45.
[8] Fraser A et al Vaccine 2007 Nov. 7; 25(45):7848-57.
[9] Sack D A et al Infect Immun 1997 June; 65(6):2107-11.
[10] McKenzie R et al. Vaccine 2008 Aug. 26; 26(36):4731-9.
[11] Foster J W. Nat Rev Microbiol 2004 November; 2(11):898-907.
[12] Edwards A D, Slater N K. Vaccine 2008 Aug. 30.
[13] Garmory H S et al. Infect Immun 2005 April; 73(4):2005-11.
[14] Honda Y, Nakano M. Chem Pharm Bull (Tokyo) 2000 July; 48(7):978-81.
[15] Levine M M, et al Lancet 1990 Oct. 13; 336(8720):891-4.
[16] A. D. Edwards, N. K. Slater Vaccine 27(29) (2009) 3897-3903.
[17] H. L. Bullifent et al Vaccine 19(9-10) (2000) 1239-1245.

The invention claimed is:

1. A method of immunization, or immunotherapy comprising:
orally administering a solid formulation comprising a therapeutically effective amount of dried viable *Salmonella enterica* vaccine cells and at least 25% (w/w) cholestyramine to a human individual in need thereof, wherein the solid formulation is covered with an enteric coating, and said coating dissolving in the intestine to release the *Salmonella enterica* vaccine cells into the upper small intestine of the human individual.

2. The method according to claim 1, wherein the dried viable cells of the *Salmonella enterica* vaccine are produced by increasing the intracellular level of a disaccharide in the cells and drying the cells in the presence of a carbohydrate stabilizing agent.

3. The method according to claim 2, wherein the disaccharide and the carbohydrate stabilizing agent are trehalose.

4. The method according to claim 1, wherein the solid formulation comprises a core which comprises granules of the dried viable bacterial cells of the *Salmonella enterica* vaccine and granules of the cholestyramine.

5. The method according to claim 1, wherein the solid formulation comprises a core which comprises viable dried bacterial cells of the *Salmonella enterica* vaccine; said core being surrounded by a layer comprising the cholestyramine.

6. The method according to claim 1, wherein the dried viable cells of the *Salmonella enterica* vaccine are lysozyme sensitive.

7. The method according to claim 6, wherein the solid formulation further comprises a cation exchange resin.

8. The method according to claim 1, wherein the dried viable cells of the *Salmonella enterica* vaccine comprise heterologous nucleic acid.

9. The method according to claim 8, wherein the heterologous nucleic acid encodes an exogenous antigen.

10. The method according to claim 1, wherein the dried viable cells of the *Salmonella enterica* vaccine and the cholestyramine are encapsulated in a polymeric shell.

11. The method according to claim 10, wherein the polymeric shell comprises hydroxypropyl methylcellulose.

12. The method according to claim 1, wherein the solid formulation comprises:

a core which comprises the dried viable bacterial cells of the *Salmonella enterica* vaccine and cholestyramine; and an enteric coating which surrounds the core.

13. The method according to claim 12, wherein the core is encapsulated in a polymeric shell which is coated with said enteric coating.

* * * * *